United States Patent

Cai et al.

Patent Number: 5,484,923
Date of Patent: Jan. 16, 1996

[54] PROCESS OF MAKING SPIROCYCLES AND ANALOGS THEREOF

[75] Inventors: Dongwei Cai, Edison; Richard Desmond, Bridgewater; Yao-Jun Shi, Edison; David M. Tschaen, Holmdel; Thomas R. Verhoeven, Cranford, all of N.J.

[73] Assignee: Merck & Co., Inc., Rahway, N.J.

[21] Appl. No.: 250,972

[22] Filed: May 31, 1994

Related U.S. Application Data

[63] Continuation-in-part of Ser. No. 75,196, Jun. 10, 1993, abandoned.

[51] Int. Cl.⁶ ............ C07D 451/10; C07D 451/107
[52] U.S. Cl. ................ 546/17; 546/15; 546/16; 546/18
[58] Field of Search ................ 546/15, 16, 17, 546/18; 514/278

[56] References Cited

U.S. PATENT DOCUMENTS

| 4,943,635 | 7/1990 | Corey | 546/13 |
| 5,206,240 | 4/1994 | Baldwin | 514/231.5 |

OTHER PUBLICATIONS

Carey et al "A new system for catalytic evautio–selective reduction" Tetrahedron Lett 31 611–614 (1990).

*Primary Examiner*—Ceila Chang
*Attorney, Agent, or Firm*—Francis P. Bigley; Mark R. Daniel

[57] ABSTRACT

The present invention is directed to a process of making spirocycles of general structural formula:

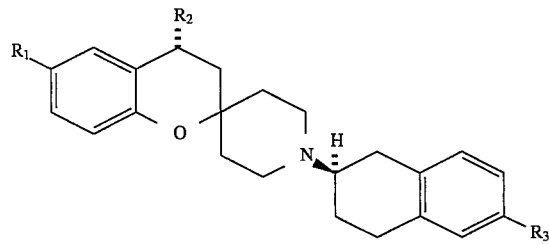

where $R_1$ is selected from the group consisting of $CO-C_{1-3}$ alkyl, cyano, carboxy, carboxy $C_{1-6}$ alkyl ester, carboxamide, $C_{1-6}$ alkyl sulfinyl, $C_{1-6}$ alkyl sulfonyl, $C_{1-6}$ methanesulfonamide and halogen; $R_2$ is selected from the group consisting of keto or alcohol, $R_3$ is cyano, resulting in compounds which are Class III antiarrhythmic.

2 Claims, No Drawings

PROCESS OF MAKING SPIROCYCLES AND ANALOGS THEREOF

CROSS REFERENCE

This is a continuation-in-part from U.S. patent application Ser. No. 08/075,196, which was filed on Jun. 10, 1993, now abandoned.

BACKGROUND OF THE INVENTION

Spirocycles of general structural Formula I:

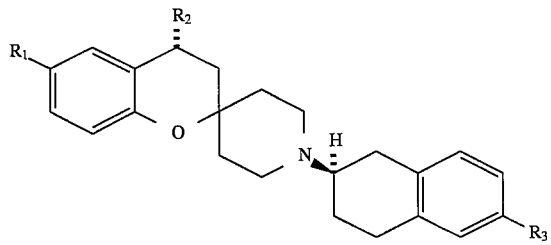

where $R_1$ is selected from the group consisting of acyl such as $CO-C_{1-3}$ alkyl, cyano, carboxy, carboxy $C_{1-6}$ alkyl ester, carboxamide, $C_{1-6}$ alkyl sulfinyl, $C_{1-6}$ alkyl sulfonyl, $C_{1-6}$ methanesulfonamide and halogen; $R_2$ is selected from the group consisting of keto or alcohol, $R_3$ is cyano, are compounds which are Class III antiarrhythmic agents.

Antiarrythmic agents of Class III are drugs which cause a selective prolongation of the duration of the action potential without a significant depression of the $V_{max}$. Drugs in this class are limited. Examples such as sotalol and amiodarone have been shown to possess Class III properties. Sotalol also possesses Class II effects which may cause cardiac depression and be contraindicated in certain susceptible patients. Also, amiodarone is severely limited by side effects. Drugs of this class are expected to be effective in preventing ventricular fibrillation. Pure Class III agents, by definition, are not considered to cause myocardial depression or an induction of arrhythmia due to the inhibition of the action potential conduction as seen with Class I antiarrhythmic agents.

A number of antiarrhythmic agents have been reported in the literature, such as those disclosed in:

(1) EP 397,121-A,
(2) EP 300,908-A,
(3) EP 307,121,
(4) U.S. Pat. No. 4,629,739,
(5) U.S. Pat. No. 4,544,654,
(6) U.S. Pat. No. 4,788,196,
(7) EP application 88302597.5,
(8) EP application 88302598.3,
(9) EP application 88302270.9,
(10) EP application 88302600.7,
(11) EP application 88302599.1,
(12) EP application 88300962.3,
(13) EP application 235,752,
(14) DE 3633977-A1,
(15) U.S. Pat. No. 4,804,662,
(16) U.S. Pat. No. 4,797,401,
(17) U.S. Pat. No. 4,806,555,
(18) U.S. Pat. No. 4,806,536.

Compounds of similar structure are found in Japanese patent publication 88-63533-B of Daiichi Pharmaceutical Co.; *J. Med. Chem.*, 19, 1315 (1976) by Bauer et al.; Iorio et al. in *Il. Farmaco-Ed Sci.*, 32, 212–219 (1977): Houlihan et at., U.S. Pat. No. 3,686,186; Davis et at., U.S. Pat. No. 4,420,485; Kealey, U.S. Pat. No. 4,810,792; Parham et al., *J. Org. Chem.*, 41, 2629 (1976). None of the compounds disclosed in the foregoing references are alleged to have antiarrhythmic activity.

SUMMARY OF THE INVENTION

A novel process for the production of the compound of Formula I

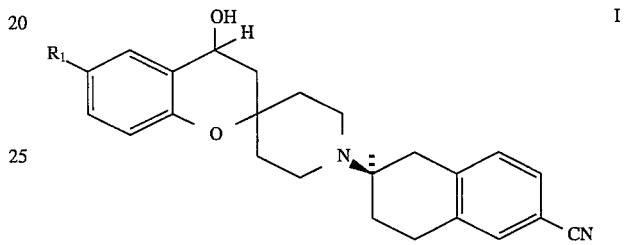

wherein $R_1$ is selected from the group consisting of acyl such as $CO-C_{1-3}$ alkyl, cyano, carboxy, carboxy $C_{1-6}$ alkyl ester, carboxamide, $C_{1-6}$ alkyl sulfinyl, $C_{1-6}$ alkyl sulfonyl, $C_{1-6}$ methanesulfonamide and halogen; comprising in order the steps of reacting 4-bromophenylacetic acid with oxalyl chloride to produce 4-bromophenylacetyl chloride; reacting the 4-bromophenylacetyl chloride of (a) with aluminum chloride to produce the aluminum addition salt of 4-bromophenylacetyl chloride; reacting the aluminum addition salt of 4-bromophenylacetyl chloride with ethylene gas to produce 6-bromo-β-tetralone of Formula X;

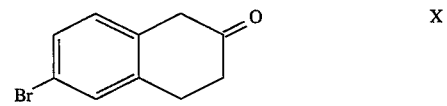

reacting the 6-bromo-β-tetralone of Formula X with piperidone ketal of Formula XI to produce the piperidone ketal of Formula XI;

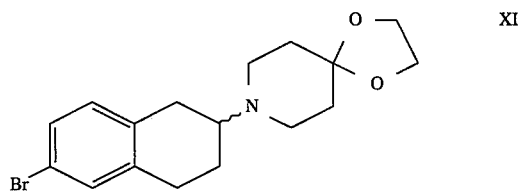

resolving the piperidone ketal of Formula XI by recrystallization with (+)Di-p-toluoyl-D-tartaric acid; debrominating and cyanating the resolved piperidone ketal of Formula XI; hydrolyzing of the resolved piperidone ketal of Formula XI with hydrochloric acid in water to produce the 3-cyano-5,6,8-dihydro-7-piperidone naphthalene of Formula XII;

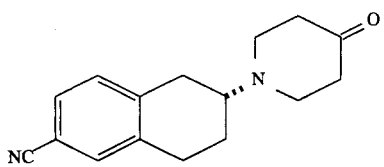

reacting p-anisidine of Formula VI and acetic anhydride to produce N-acetyl-p-anisidine of Formula VII; reacting the N-acetyl-p-anisidine of Formula VII with acetyl chloride; reacting the product of (b) with aluminum chloride to produce 5-acetamido-2-hydroxyacetophenone of Formula VIII; reacting the 5-acetamido-2-hydroxyacetophone of Formula VIII with hydrogen chloride to produce the hydrochloride salt of Formula VIII; reacting the hydrochloride salt of Formula VIII with methanesulfonyl chloride to produce acetophenone mesylate of Formula V;

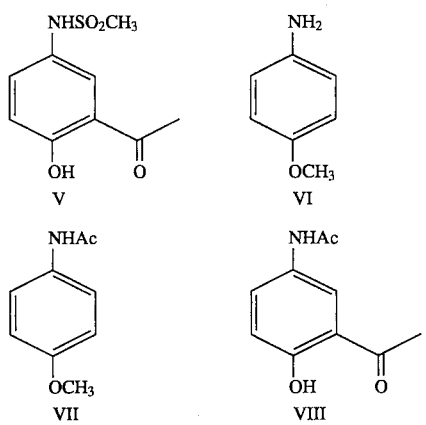

reacting acetophenone mesylate of Formula V and a cyanopiperidone ketone of Formula IV to produce the compound of Formula II;

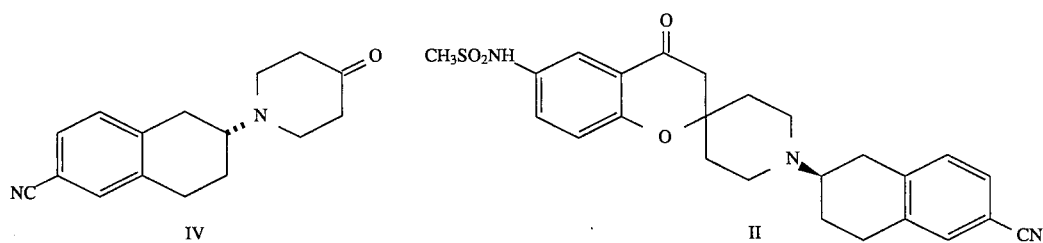

and reducing a compound of Formula II with oxazaborolidine borane complex in the presence of IPA. This novel process for the debromination and cyanation utilizes zinc cyanide as the source of cyanide ion which has unexpectedly been found to result in greater efficiency and yield in this process. Further, this novel process involves the reduction of an aromatic ketone using oxazaborolidine-borohydride and dimethylsulfide-borohydride in methylene chloride which contains 1–3 equivalents.

Preparation of compounds of Formula I is achieved via a four step synthesis. In Step 1, synthesis of the cyanopiperidone ketone intermediate is accomplished using the following reaction sequence.

STEP 1

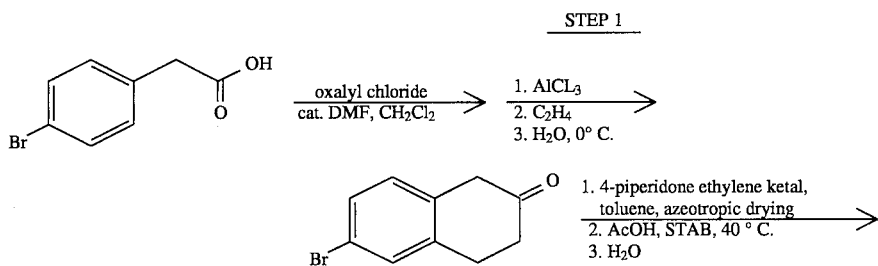

-continued
STEP 1
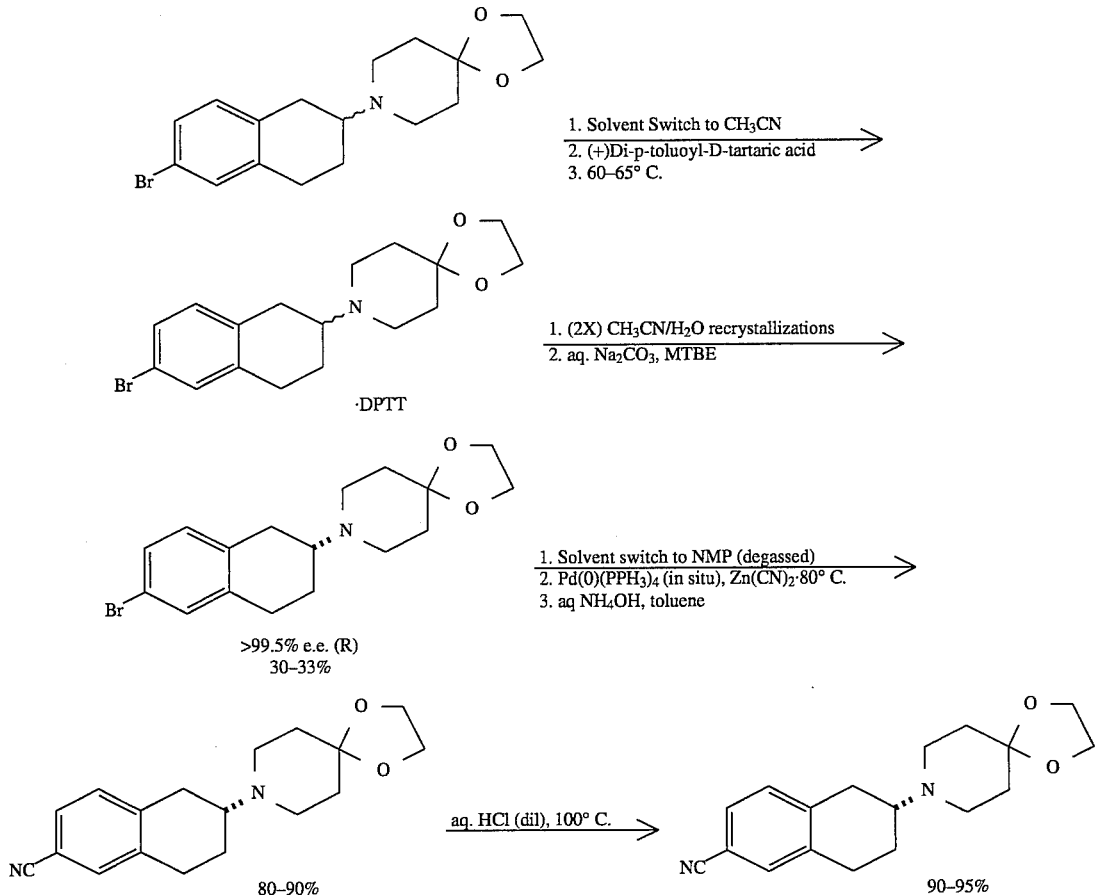
Next in Step 2, the appropriate 2-hydroxyacetophenone is synthesized using the following general reaction scheme which shows the synthesis of the 5-sulfonamido compound.
STEP 2
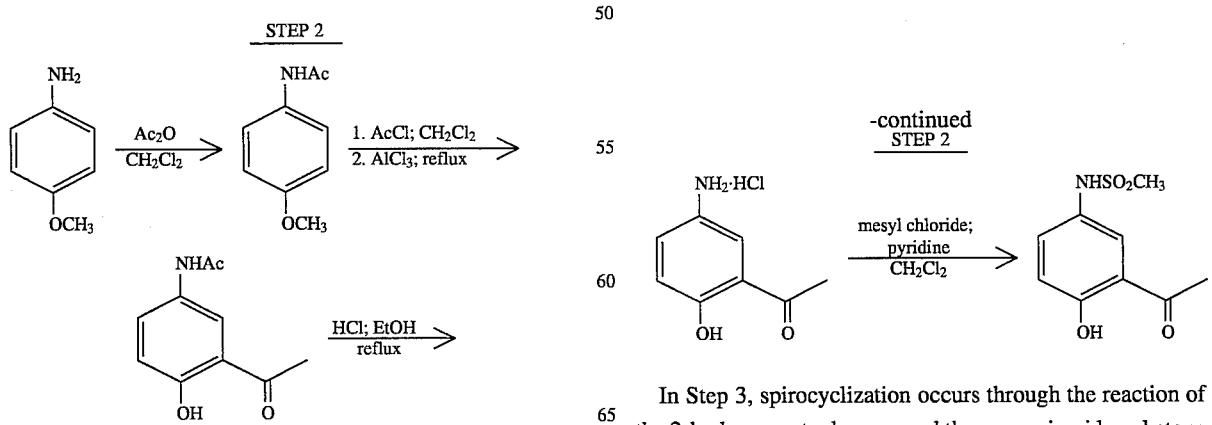
In Step 3, spirocyclization occurs through the reaction of the 2-hydroxyacetophenone and the cyanopiperidone ketone as follows:

STEP 3
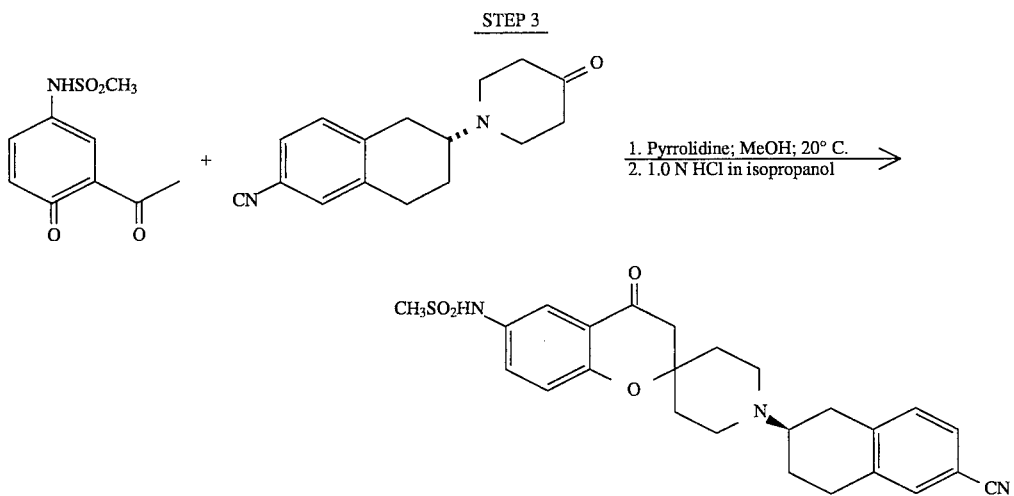
Step 4 results in the reduction of the ketospirocycle to the alcohol. This is accomplished through the following reaction steps:
STEP 4
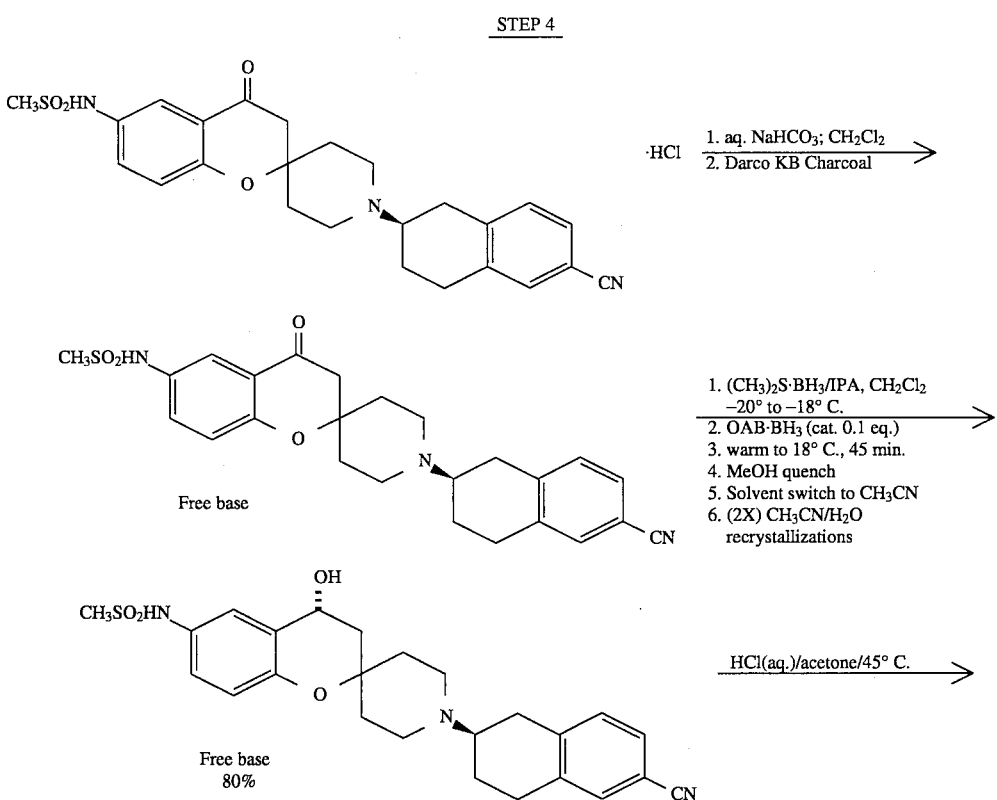

-continued
STEP 4

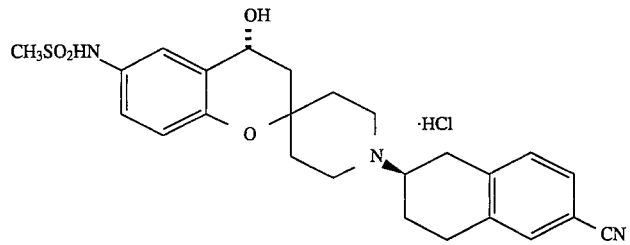

The novel use of Zn(CN)$_2$ rather than the other more soluble cyanides results in an unexpectedly high yield during the debromination and cyanation reaction. Additionally, the use of isopropanol as a co-solvent in the reduction process resulted in an unexpectedly high stereoselectivity.

DETAILED DESCRIPTION OF THE INVENTION

The present invention is directed to a process of making spirocycles of general structural formula:

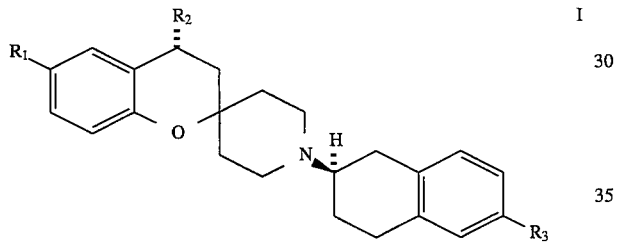

where R$_1$ is selected from the group consisting of acyl such as CO—C$_{1-3}$ alkyl, cyano, carboxy, carboxy C$_{1-6}$ alkyl ester, carboxamide, C$_{1-6}$ alkyl sulfinyl, C$_{1-6}$ alkyl sulfonyl, C$_{1-6}$ methanesulfonamide and halogen; R$_2$ is selected from the group consisting of keto or alcohol, R$_3$ is cyano, resulting in compounds which are Class III antiarrhythmic agents.

Preparation of compounds of Formula I is achieved via a four step synthesis. In Step 1, synthesis of the cyanopiperidone ketone intermediate is accomplished using the following reaction sequence

STEP 1

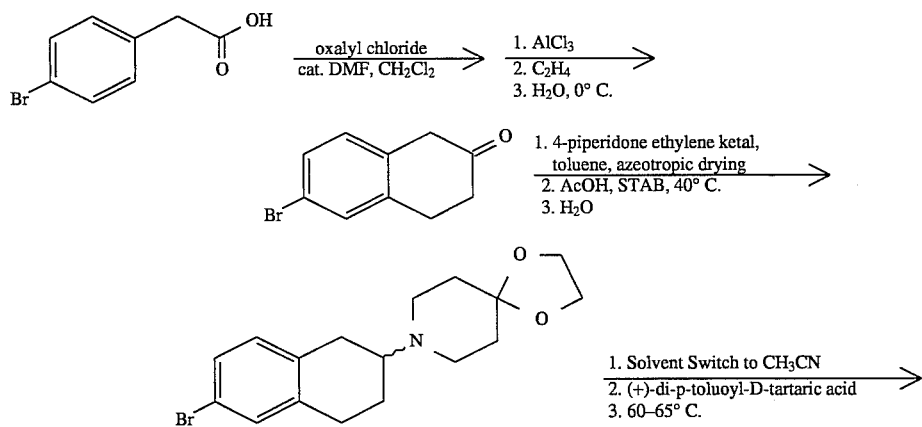

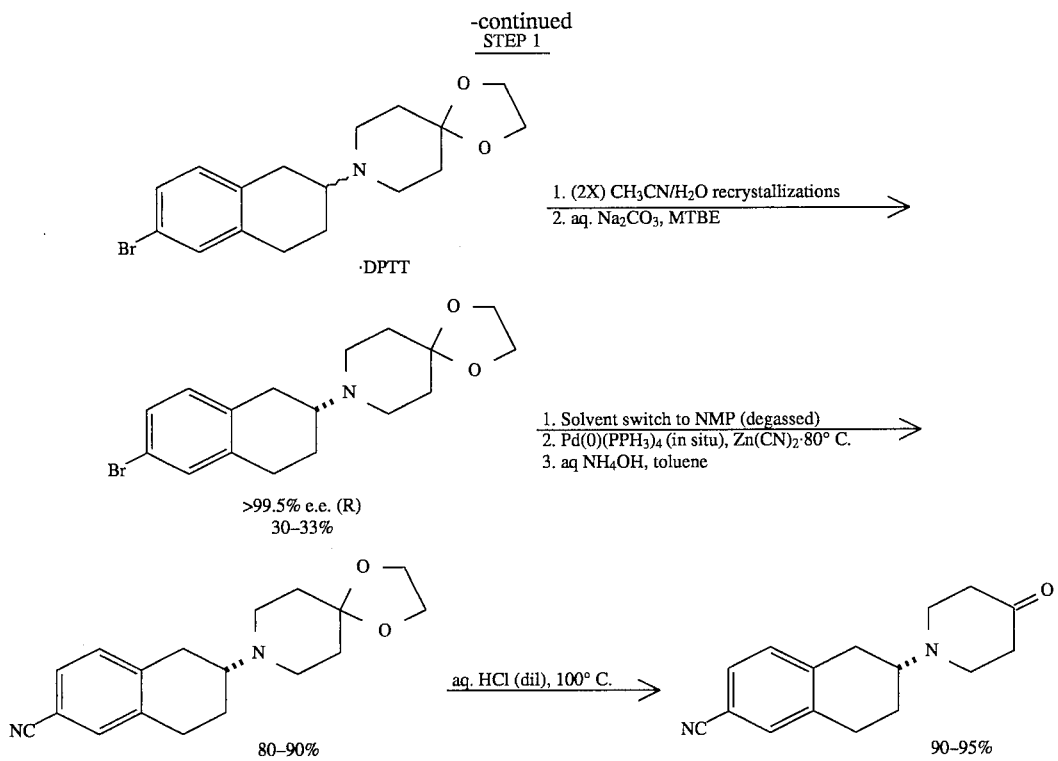

The synthesis of 6-bromo-β-tetralone is accomplished by dissolving 4-bromophenylacetic acid in methylene chloride and dimethyl formamide, under nitrogen. Oxalyl chloride is added and the mixture is stirred under a positive nitrogen atmosphere to produce the 4-bromophenylacetyl chloride, at a yield which typically is better than 99%.

The ethylene addition reaction is accomplished by first reacting AlCl$_3$ with the acid chloride to produce the aluminum addition salt, and then adding the ethylene gas. The addition and ring closure reactions are allowed to proceed until approximately 2% of the starting material remains (by HPLC). The reaction is then quenched with the addition of cold (0° C.) water.

The 6-bromo-β-tetralone is then reacted with piperidone ethylene ketal in the presence of acetic acid and STAB (sodium triacetoxyborohydride) in methylene chloride and toluene. This reaction generally produces a yield of about 85%. The (+)Di-p-toluoyl-D-tartaric acid salt of the bromamineketal is then produced and the stereospecific product is recrystalized from acetonitrile and water.

In a preferred embodiment, N-{1'(6-cyano-1,2,3,4-tetrahydro- 2(R)-napthalene)-3,4-dihydro-4(R)hydroxyspiro(2H-1-benzopyran- 2)-4'-piperidine]-6yl is produced using this novel process.

In an other embodiment, the invention concerns a process of dehalogenation and cyanation of aryl compounds. The replacement of the bromide with cyanide is accomplished with unexpected efficiency using zinc cyanide in the presence of a catalytic amount of palladium (0). The use of palladium (0) catalysis in aryl cyanation reactions is documented in the literature. The reactions however, typically employ aryl iodides or triflates as substrates for cyanation. Aryl bromides are known to be substantially less reactive toward cyanation. (See for example K. Takagi et at., *Bull Chem. Soc. Jpn.*, 1991, 64, 1118.

Attempts to effect conversion of the bromamineketal using potassium cyanide and palladium(O) led to little or no product formation. Addition of alumina as a co-catalyst was also ineffective. The reaction was then carried out using zinc cyanide with palladium(O) catalysis and assay yields of 90–95% were obtained for the conversion. In addition, unexpectedly it was determined that the reaction goes to completion with only 0.6 molar equivalents of zinc cyanide which indicates that both cyanides are transferred from zinc.

In a manner similar to the above cyanation of aryl iodides has also been accomplished using this procedure. Cyanation of aryl iodides was shown to occur more rapidly than the corresponding aryl bromide.

In Step 2, the appropriate 2-hydroxyacetophenone is synthesized using the following general reaction scheme which shows the synthesis of the 5 sulfonamido compound.

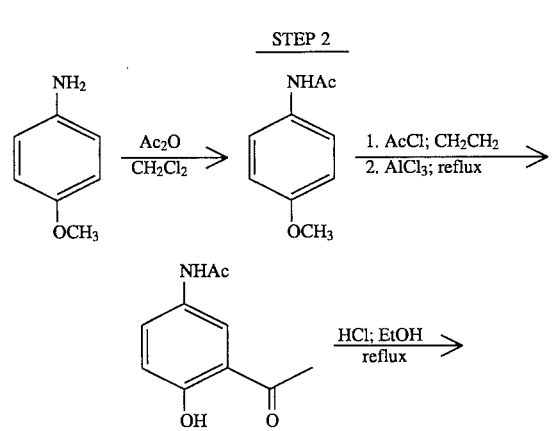

-continued
STEP 2

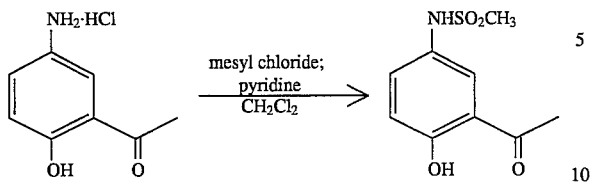

As is appreciated by those of ordinary skill in the art, mesyl chloride is used here to exemplify the reaction.

In Step 3, spirocyclization occurs through the reaction of the 2-hydroxyacetophenone and the cyanopiperidone ketone as follows:

STEP 3

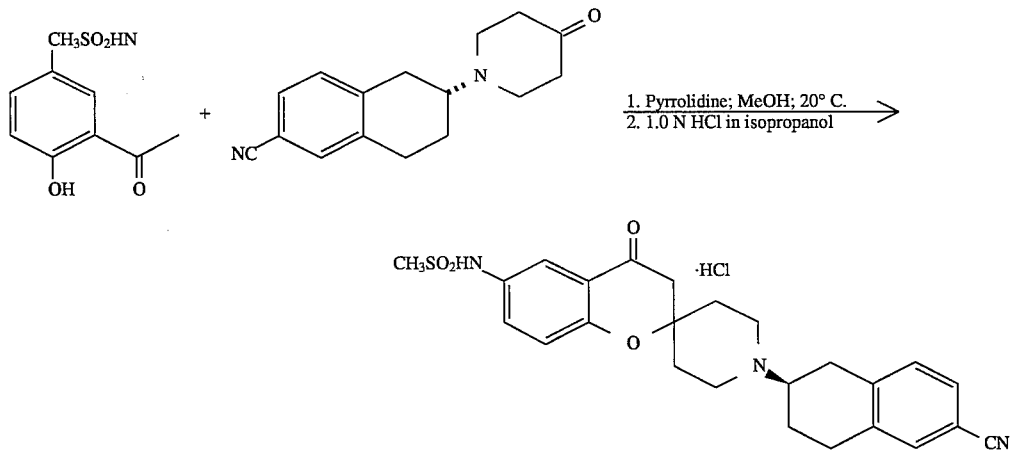

In Step 4 the reduction of the ketospirocycle to the alcohol is accomplished. This is accomplished through the following reaction steps:

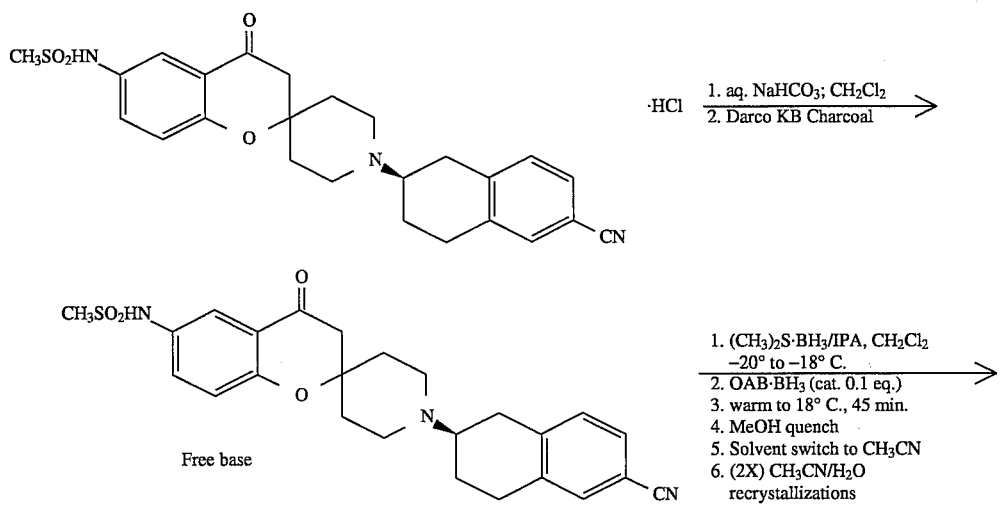

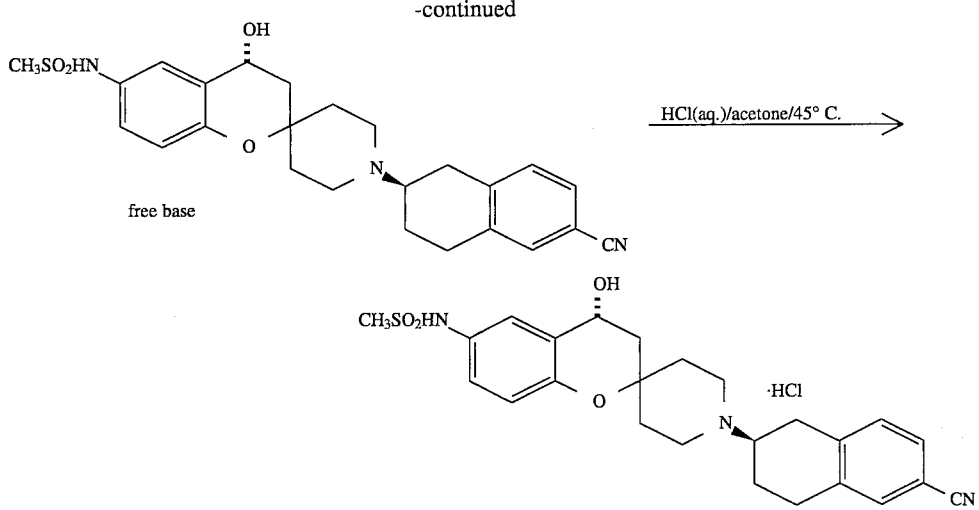

While there are several methods for chiral reduction of ketones (see for example the review by V. K. Singh, *Synthesis*, 1992, 605–617), the oxazaborolidine (OAB) reagents (E. J. Corey et al., *J. Am. Chem. Soc.*, 1987, 109, 5551–5553; and *J. Am Chem. Soc.*, 1987, 109, 7925–7926; as well as S. Itsuno et al., *J. Org. Chem.* 1984, 49, 555–557; and *S. Bull Chem Soc. Jpn.*, 1987, 60, 395) offer a stable reagent (See U.S. Pat. No. 5,039,802) with good to excellent stereoselectivites. Further elaboration of this methodology has been presented in U.S. Pat. Nos. 5,039,802 and 5,189,177 which issued to Blacklock, et al.

Treatment of the ketone with 1 mole equivalent of borane methyl sulfide lead to a stable 1:1 borane amine complex which could be isolated and characterized by NMR. Treatment of this complex with 0.5 mole of OAB.BH₃ lead to complete conversion to the desired alcohol. However, the stereoselectivity of this reaction was significantly lower (92%) than desired.

To investigate this further, the reduction of model ketones, shown in Table 1, using 0.6–0.7 equivalents of OAB.BH₃ were studied. In an effort to increase the stereoselectivity, the asymmetric reduction of these model ketones was carried out a second time in the presence of 1 equivalent of tertiary amine (triethylamine) using 1.2 to about 1.5 equivalents of OAB.BH₃ reagent. The results which are shown in Table 1 indicate that the enantioselectivity of the reduction is significantly enhanced by the addition of 1 equivalent of triethylamine.

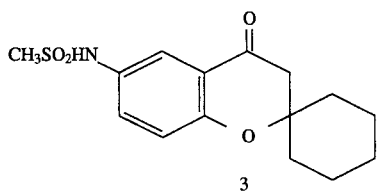

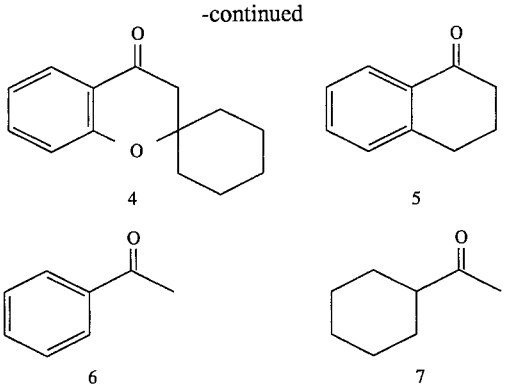

TABLE 1

| Ketones | 3 | 4 | 5 | 6 | 7 |
|---|---|---|---|---|---|
| OAB.BH₃, % ee | 90 | 91 | 90 | 96 | 67 |
| OAB.BH₃ and Et₃N, % ee | 99.1 | 99.4 | 99.4 | 99.2 | 87 |

All reactions were run at −15° C., OAB.BH₃ was added either as a solid or a solution to a solution of ketone or ketone with triethylamine. The alcohols were isolated by silica gel flash chromatography and characterized by NMR, and enantioselectivities were determined by making the Mosher esters of resulting alcohols and racemic alcohols assayed by HPLC using normal phase Zorbax silica column.

Reacting acetophenone and triethylamine with OAB.BH₃, the formation of monoalkoxyborane triethylamine complex could be studied at room temperature by NMR. Using NMR to monitor the reaction of acetone with OAB.BH₃ at −80° C. indicated an extremely rapid transfer of one hydride resulting in a monoisopropoxyborane oxazaborolidine complex (1:1 adduct) which was quite stable at −80° C. That is, by trapping the reactive intermediate free monoalkoxyborane or monoalkoxyborane oxazaborolidine complex with triethylamine, the enantioselectivity of the asymmetric reduction was significantly improved.

Likewise, the enantioselectivity of these reductions is unexpectedly improved by the addition of isopropanol (IPA) to the reaction mixture as shown in Table 2. The enhancement of the enatioselectivity of these reductions by the addition of TEA or IPA is unprecedented. The reaction of alcohols with boranes is well know. Although this should preclude the use of alcohols, such as isopropanol, in fact, as shown in Table 2, the enantioselectivity is improved.

TABLE 2

| Ketones | 4 | 8 | I |
|---|---|---|---|
| OAB.BH$_3$, % ee | 88 | 89 | 92 |
| OAB.BH$_3$ and IPA, % ee | 95 | 94 | 98 |

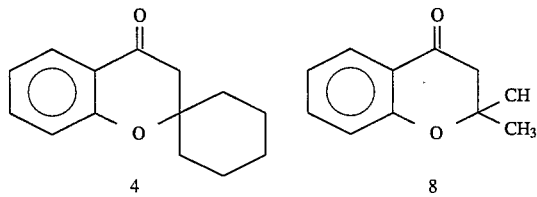

4    8

EXAMPLES

The following examples illustrate the present invention and as such are not to be considered as limiting the invention set forth in the claims appended thereto.

Example 1

Synthesis of 6-halo-β-Tetralone

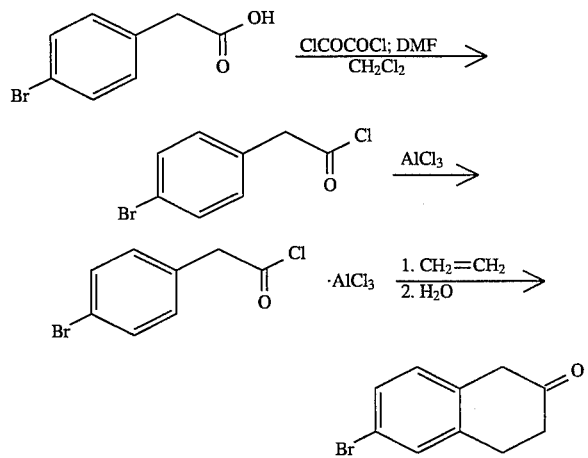

The process for the preparation of 6-bromo-B-tetralone was as follows. The reaction vessel was charged with 48.0 g of 4-bromophenyl-acetic acid followed by 480 mL of methylene chloride. These were stirred while sweeping the vessel with nitrogen, to give a clear amber solution. DMF, 0.359 mL, was then added to the solution in a single portion. Oxalyl chloride, 22.0 mL, was added drop-wise to the clear amber solution over 6 hours under positive nitrogen pressure (not a sweep). During the addition, an acidic gas was evolved from the aqueous mixture. The gas evolution continued for up to 1.5 hours after complete addition of the oxalyl chloride. The reaction solution turned clear yellow, and was allowed to age for an additional 14–18 hours while stirring gently under positive nitrogen pressure. The conversion from the 4-bromophenyl-acetic acid to the 4-bromophenylacetyl chloride is typically better than 99% (NMR).

Following the age period, the reaction solution was cooled to 0° C. Aluminum trichloride, 32.74 g, was charged to the clear yellow solution in several portions, temporarily raising the temperature to 3°–4° C. during the addition. After the addition, the reaction mixture was a brown solution.

The ethylene addition was carried out in a sealed autoclave with an external cooling jacket that was set to circulate at 8° C. Internal vessel temperature prior to ethylene addition was between 10° and 12° C. Ethylene was added using a constant pressure of 5 psi while stirring at 1500 rpm, causing an initial exotherm of 5°–10° C. Ethylene uptake, monitored by a gasometer, is also very rapid at first, but decreases quickly after this initial surge until it nearly ceases altogether. Temperature also declines in an almost parallel manner to the decrease in the rate of ethylene consumption and eventually returns to its baseline value. The reaction is monitored by LC to determine if the amount of remaining starting material is within acceptable limits (typically less than 2 A%).

The brown reaction mixture (under nitrogen) is cooled to 0°–2° C. and then slowly quenched into an equal volume of cold (0° C.) water while rapidly stirring. The rate of the quench is controlled so that the temperature of the quenched solution stays below 10° C. After the quench is complete the two-phase solution is stirred vigorously for several hours and allowed to warm up to room temperature in order to break up the emulsions that form during the quench. The two layers are allowed to separate, resulting in a clear, colorless aqueous phase (pH≈2) on the top and a mostly clear, yellow organic phase on the bottom. A small amount of gray solids are usually suspended at the interface between the two phases. The layers are separated, keeping the solids with the aqueous phase, and the aqueous phase is washed with a small amount of methylene chloride (about 20% of total aqueous volume). The wash is added to the organic phase, and the combined solutions is filtered in order to remove any insoluble particles. Yield of the product, 6-bromo-β-tetralone, averaged about 89%. The crude product solution is clear yellow and is carried directly into Example 2.

Example 2

Preparation of bromo amine ketal

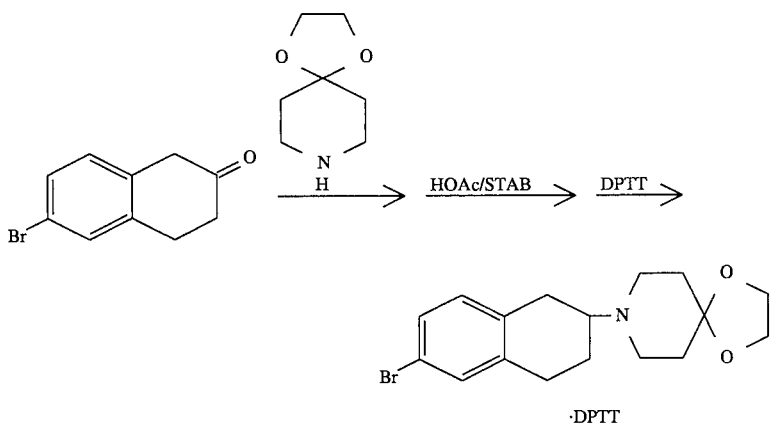

The methylene chloride solution (230 mL) containing the 6-bromo-β-tetralone, prepared in Example 1, was concentrated to 80 mL total volume. Piperidone ethylene ketal, 9.4 mL, 1.05 molar equivalents) was added and the mixture heated to reflux with water removed azeotropically using a Dean Stark trap for 1.5 hours. Analysis of the resulting solution showed no starting material following the removal of water.

The mixture was then concentrated in vacuo to a volume of 100 mL. Dry tetrahydrofuran (K.F.<75 ug/ml, 150 mL) was added, followed by acetic acid (10 mL, 2.5 molar equivalents) and 19.2 g of sodium triacetoxyborohydride (STAB). There was usually a slight exothermic response during the addition of STAB.

The batch was then heated to 45° C. for 16 hours. HPLC assay showed no starting material at the end of this time period. The mixture was cooled to room temperature and poured into 100 mL of ice water. Next, 100 mL of MTBE was added and the mixture was stirred for 5 minutes. The pH of the mixture was then adjusted to 8.0 using aqueous sodium carbonate solution. The solution was then concentrated to 100 mL. Acetonitrile, 100 mL, was added and the concentration procedure is continued until the volume is reduced to 75 mL. This concentration procedure was repeated a second time since it is critical that all of the toluene present be displaced.

The concentrated solution was diluted to 400 mL total volume with acetonitrile and heated to 50° C. (+)Di-ptolyl-tanarric acid, 26.9 g) was then dissolved in 50 mL of acetonitrile and added. The batch was then aged at 50° C. for 10 minutes and cooled to 20° C. over 30 minutes. After aging at 20° C. for three hours, the mixture was filtered and the cake washed with 75 mL of acetonitrile. The cake, was then used in Example 3.

Resolution of the enantiomeric forms was accomplished by producing the bromoamine ketal (+)Di-p-toluoyl-D-tartaric acid salt. This was accomplished by mixing 18.0 g of tartrate salt in 630 mL of acetonitrile containing 5% water. The resultant slurry was heated to reflux (approximately 78° C.) to give a pale orange solution which remained slightly cloudy. After 5 minutes at reflux, the heat was removed and the solution was allowed to cool to room temperature under a nitrogen atmosphere. The tartrate salt started crystallizing at 53°-50° C. The resulting slurry was aged at 21 ° C. for four hours. The tartrate salt was isolated by filtration and the cake washed with 100 mL of acetonitrile. The salt was air dried overnight.

In a second recrystallization, 15.73 g of tartrate salt was suspended in 550 mL of acetonitrile containing 5% water and heated to reflux to produce a clear but slightly pale yellow solution. The Solution was allowed to cool to room temperature and the tartrate salt crystallized from the hot 65°-60° C. solution. The resulting slurry was aged overnight. The salt was isolated by filtration and the cake was washed with 100 mL of acetonitrile and air dried.

Neutralization of the tartrate salt was accomplished by suspending the salt in 150 mL of MTBE. The suspension of tartrate salt was treated with 125 mL of an aqueous solution containing 10.8 g of sodium carbonate. The mixture was stirred for 15 minutes and the layers separated. The MTBE was washed with one 50 mL portion of water. At this is point the MTBE solution became slightly cloudy. The MTBE phase was concentrated in vacuo and the solvent was switched to 60 mL of NMP. The bromoamine ketal/NMP solution contained 11.90 g of bromoamine ketal by HPLC quantification.

Example 3

Cyanation Procedure

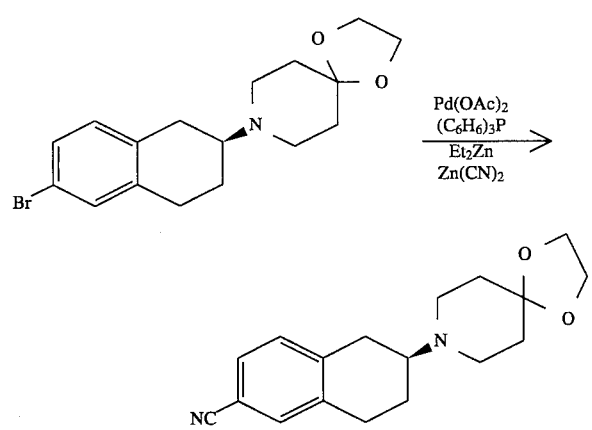

The catalyst was prepared by combining 228 mg of palladium acetate (Pd(OAc)$_2$ and 1.20 g of triphenylphosphine (Ph$_3$P) in 20 mL of NMP. The resulting solution was degassed with vacuum and vented to nitrogen. The solution was heated at 50° C. for 30 minutes, followed by the addition of 1.52 mL of diethyl zinc (Et₂Zn). The resulting bright yellow solution was heated at 50° C. for 30 minutes.

The bormoamine ketal solution in NMP (from the previous step) was degassed with vacuum and vented to nitrogen. The degassed solution was transferred via cannula to the 50° C. catalyst solution and aged at 50° C. for 10 minutes. The solution was treated with 2.19 g of zinc cyanide (Zn(CN)₂) using a solids addition funnel to maintain the inert atmosphere. The resulting yellow solution with solid zinc cyanide was heated at 80° C. for 4 hours. Subsequent studies have demonstrated that the reaction will proceed at temperatures between 70° and 100° C. (The reaction was monitored by HPLC for the disappearance of the starting material.)

The reaction mixture was diluted with 50 mL of toluene and filtered. The filtered solution was added to a rapidly stirring mixture of 125 mL of 15% concentrated ammonium hydroxide in water (v/v) and 75 mL of toluene at 19° C., with the temperature allowed to rise to 30° C. The mixture was stirred for 1 hour while cooling to room temperature. The layers were separated and the organic layer was washed with 75 mL of water and 75 mL of brine. The toluene solution contained 9.14 g of cyanoamine ketal by quantitative HPLC assay. This was a yield of 90.6%.

Deketalization was accomplished as follows.

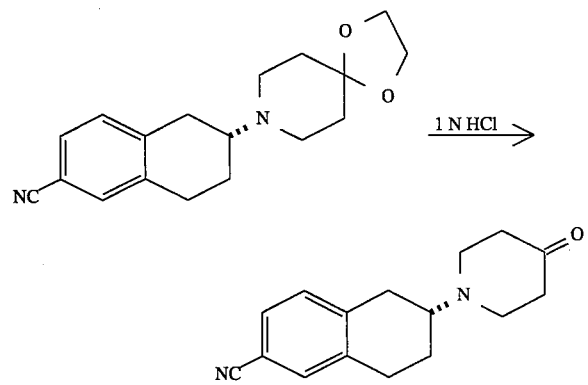

the toluene solution containing the cyanoamine ketal was extracted with 250 mL of 1N HCl. The 1N HCl solution of the cyanoamine ketal was washed with 50 mL of toluene and filtered. The filtered solution was diluted with 890 mL of 1N HCl (concentration 1 g/125 mL) and heated at 95° C. for 2 hours. (The reaction was monitored by HPLC, at completion, typically 0.2–0.4 area % of the starting material remained.) The solution was cooled to room temperature and 50% sodium hydroxide solution was added to bring the mixture to pH 8.5 to 9.0. During the addition the temperature was maintained below about 25° C. with external cooling. The resulting thick white slurry was aged for 1 hour at room temperature. The product was isolated by filtration and the cake was washed with 200 mL of water. The cyanoaminelatone was dried in vacuo at 40° C. with a nitrogen sweep to yield 7.5 g of cyanoamineketone (96% yield) as a tan solid.

Example 4

Preparation of 2-hydroxy-5-methanesulfonamido acetophenone

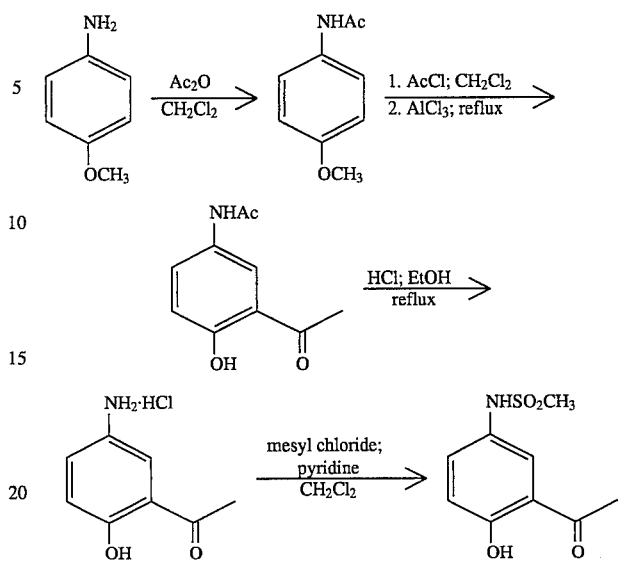

The 5-substituted-2 hydroxyamido is prepared from p-Anisidine. A suspension which contained 100 g of p-aniside was prepared in 350 mL tetrahydrofuran (<300 uL of water/mL by KF). A total of 77 mL of acetic anhydride was added slowly while maintaining a temperature less than 30° C. using an ice bath. The reaction was aged at 25° C. for 1.5–2 hours and was monitored using an HPLC assay which comprised a C-8 column, with a flow rate of 1.5 mL/min and a linear solvent gradient consisting of acetonitrile, water and phosphoric acid initially at a ratio of 20:80:0.1% and after 10 minutes achieving 35:65:0.1. An ultra violet detector, fixed at 254 nm, was used.

The reaction mixture was slowly added to 750 mL of hexane while stirring and aged for 30–45 minutes. The solids were filtered and dried in vacuo overnight to produce 122.75 g of fluffy, light purple solid N-acetyl-p-anisidine.

A Friedel-crafts reaction was used to prepare 5-acetamido- 2-hydroxyacetophenone from the N-acetyl-p-anisidine. A total of 30 mL of acetyl chloride was added all at once to a solution containing 20 g of N-acetyl-p-anisidine in 200 mL of methylene chloride (<100 µg of water/mL by KF). The solution was heated to reflux (~35° C.) at which point the N-acetyl-p-anisidine was fully dissolved. The mixture is cooled to 30° C. and 54.9 g of aluminum chloride was added in small portions over a 30 minute time period. The temperature was maintained below 35° C. during the addition of the aluminum chloride. After the addition is complete, the mixture was refluxed for 4–5 hours and the reaction was monitored by HPLC until complete. The HPLC conditions used comprised a octylsilane column with a flow rate of 1.5 mL/min of acetonitrile: water:phosphoric acid (20:80:0.1). The reaction mixture was then cooled to 20°–25° C. and quenched slowly into 424 mL of 0°–2° C. water while maintaining the batch temperature below 15° C. during the quench. The quench mixture was stirred for 15–30 minutes and then filtered. The yellow-green solids are washed twice with 25 mL portions of water and then dried in vacuo overnight to produce 15.7 g of yellow green solid which upon analysis by HPLC was shown to be >99% 5-acetamido- 2-hydroxyacetophenone.

In order to produce the 5-amino-2-hydroxyacetophenone HCl, 20 g of 5-acetamido-2-hydroxyacetophenone was suspended in 170 mL of 95% ethanol. To this suspension was rapidly added 62.2 mL of 6N hydrochloric acid (aqueous)

and the solution was heated to reflux. The mixture was refluxed for 12 hours and monitored by HPLC until complete. The reactor was monitored using HPLC analysis, comprising a octylsilane column, with a flow rate of 1.5 mL/min and a mobile phase of acetonitrile:water:phosphoric acid (20:80:0.1). A ultra violet detector, set at 254 nm, was used.

The mixture was cooled and concentrated in vacuo to a final volume of 80 mL. During vacuum concentration, the product begins to precipitate. The mixture was then stirred at 20°–25° C. for 1 hour and filtered. The cake was washed with 40 mL of acetonitrile and dried in vacuo for 16 hours at 40° C. This procedure produced 15 g of the silvery-blue solid 5-amino-2-hydroxyacetophenone hydrochloride.

A suspension containing 5 g of 5-amino-2-hydroxyacetophenone was prepared in 80 mL of THF. This suspension was cooled to 0°–5° C. and 5.2 mL of pyridine was added all at once. While stirring, 2.2 mL of methanesulfonyl chloride was added over 30 minutes. The temperature was maintained between 0°–5° C. during this addition. The batch was warmed to 20°–25° C. over at least 15 minutes and then aged at room temperature for 6–10 hours. The reaction was monitored by HPLC using an octalsilane column, with a flow rate of 1.5 mL per minute using a linear gradient system consisting of acetonitrile:water:phosphoric acid starting at 20:80:0.1 and after 10 minutes achieving 35:65:0.1. Detection was accomplished using a ultra violet detector at 254 nm.

The reaction mixture was washed with 60 mL of 1N aqueous HCl and the organic layer was separated. The organic layer was concentrated to a volume of 45 mL in vacuo. Precipitation of the N-mesylhydroxy acetophenone is initiated by adding 150 mL of hexanes drop-wise over 60 minutes and stirring the mixture for an additional 60 minutes. The solids are filtered and washed with 15 mL of hexanes and dried in vacuo. This procedure resulted in the production of 4.6 g of a fluffy, off-white solid which was identified as N-mesylhydroxy acetophenone.

Example 5

A 500 mL, 3-neck, round bottom flask was sealed with a septa and then fitted with a positive nitrogen pressure inlet and a thermocouple. A magnetic stirring bar was placed in the flask, and the flask was charged with 60 mL of methanol. Using a syringe, 2.00 mL of pyrrolidine was added rapidly to the methanol, causing a 2°–3° C. exotherm. Next, 4.00 g of N-mesylhydroxy acetophenone was added to the pyrrolidine/methanol solution in several small portions over about 1–2 minutes. A decrease in temperature of 1°–2° C. was observed following this addition, along with the production of a red-orange solution. The cyanoamine ketone, 4.00 g, was added to this solution all at once, and changed the solution to an orange slurry. This mixture was allowed to age at ambient temperature (18°–22° C.) for 23 to 26 hours. During this aging process, after approximately 2 to 3 hours, the slurry became a dark brown solution, with no visible undissolved solids.

After a qualitative determination of the solution to confirm the reaction's completion, the reaction vessel was fitted with a 60 mL pressure-equalizing addition funnel. The funnel was charged with 24 mL of 1.01N HCl in isopropanol. This HCl solution was rapidly dripped into the stirring brown reaction solution, at ambient temperature, causing a slight (2°–3° C. exotherm and generating a wispy white "smoke" in the head space above the solution. After this first addition was complete, the reaction solution was a green-brown color. This solution was heated to 40° C. The addition funnel was charged with an additional 24 mL of 1.01N HCl in isopropanol, which was added to the solution at 40° C. in the same manner described above. There was little, or no exotherm or "smoke" created during the second addition.

The green-brown solution was further heated to 60° C. Crystallization of the spirocycle HCl occurs while the solution is being heated. The resulting tan slurry is held at 60° C. for about 1 hour, then the heat source is removed and the slurry is allowed to cool to ambient temperature. The slurry is aged at 18°–20° C. for 12 to 18 hours. After aging, the slurry is filtered, and the yellow filter cake is washed with 25 mL of methanol. The cake is air-dried over vacuum for 12 to 16 hours. Quantitative HPLC, showed that the purity of the product was 96% wt %.

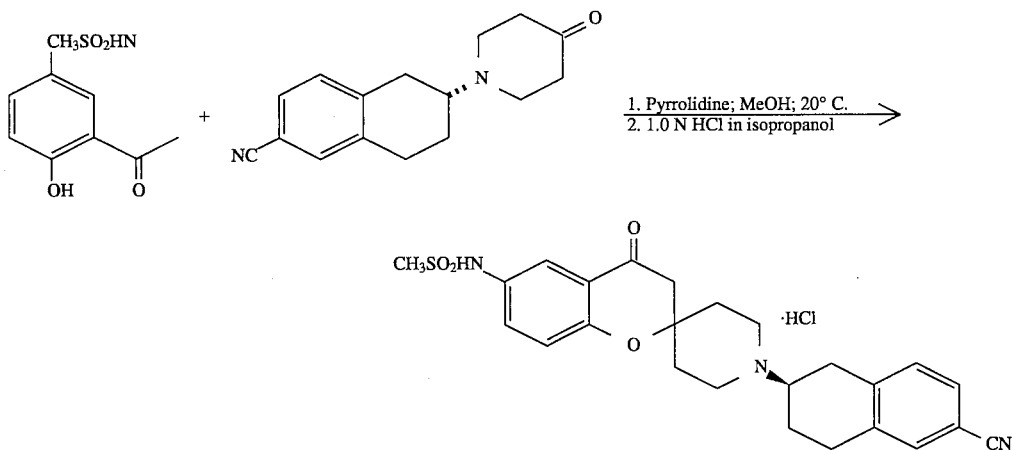

Example 6

Reduction of Ketone to Alcohol

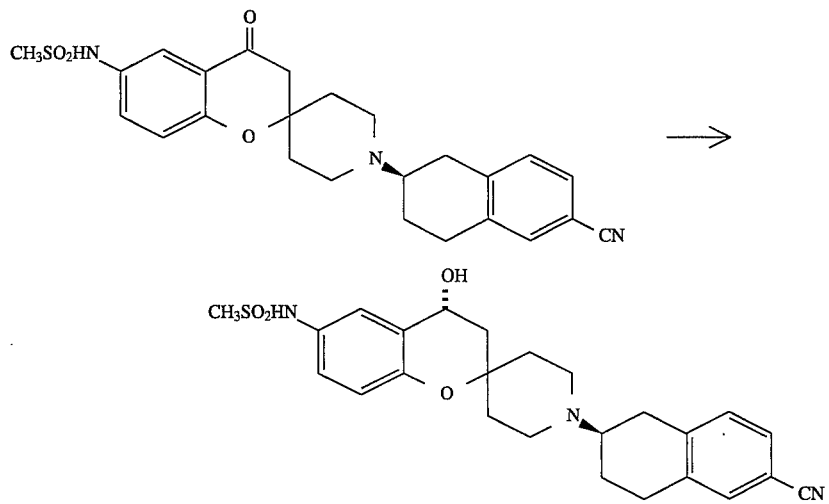

| Materials | Amount | Moles | MW |
|---|---|---|---|
| L-702,958 | 16.86 g | 0.032 | |
| 5% Sodium Bicarbonate | 163 | | |
| Methylene Chloride | 600 mL | | |
| Saturated Sodium Chloride | 82 mL | | |
| Water | 82 mL | | |
| Darco KB | 5.06 g | | |
| Isopropanol | 2.2 mL | 0.031 | 60.1 |
| Borane Methyl Sulfide | 7.49 mL | 0.076 | 75.97 |
| OAB.BH$_3$ | 0.87 G | 0.0031 | 290.99 |

To a slurry of L-702,958 (16.86 g, 0.032 moles) in methylene chloride (300 mL) was added 5% aqueous sodium bicarbonate (163 mL) at 20°–25° C. The mixture was stirred for 60 min and allowed to settle. The layers were separated and the organic layer was washed with half saturated brine (163 mL). The methylene chloride solution was then treated with Darco KB 5.06 g at 20° C. for 3 h. The carbon was removed by filtration and the cake was washed with methylene chloride (300 mL).

Carbon treatment served to reduce the level of several (2–3) late eluting impurities.

The methylene chloride solution of free base was concentrated by atmospheric distillation to a final volume of 278 mL which contained 13.9 g of the ketone as the free base.

Water determinations, using the Karal Fisher procedure, of the solution should be <50 µg/mL before proceeding. If it is >50 µg/mL, dry methylene chloride was added and distilled off to azetropically dry the batch.

The free base was typically ~99 A% pure at this point. Add the borane methyl sulfide to the methylene chloride solution.

Ispropanol (2.2 mL, 0.031 moles) was added and the mixture was cooled to −18° C. (±2° C.). The amount of isopropanol utilized may range from about 1 mole to about 3 molar equivalents. The reaction may be carried out at temperatures between about −20° C. and +20° C. The oxazaborolidine.BH$_3$ complex (0.89 g, 0.0031 moles) was added as a solid in one portion and the mixture was stirred at −18° C. (±2° C.) for 25 min and then warmed to 18° C. over 35 min. HPLC and TLC analysis after 45 min at 18° C. indicated consumption of the starting material. (HPLC analysis was conducted using a Zorbax® Rx-C8 column and an isocratic mobile phase comprising, CH$_3$CN:H$_2$O:0.1% H$_3$PO$_4$ isocratic 50:50. The flow rate was 1.0 mL/min and U.V. detection was performed at 220 nm.)

Methanol (245 mL, KF <50 gg/mL) was added and the mixture was stirred at 18° C. for 30 min. Methanol addition resulted in H$_2$ liberation.

The batch was then heated to distill off methyl sulfide (bp 38° C.), methylene chloride, and trimehtylborate (bp= 53°–58° C.). Additional methanol (250 mL) was added and the batch was ultimately heated at 63°–65° C. for 35 min in order to decompose the amine borane complex.

Decomposition of the amineoborone complex was followed by HPLC and/or TLC. HPLC analysis was conducted using the conditions previously described.

The final volume is 100 mL. Acetonitrile (100 mL) was added at 20°–25° C. and vacuum distillation was carded out to a volume of 70 mL.

The temperature during the distillation should be 25°–35° C. If too low a temperature is used, the methanol solvated alcohol free base may crystallize.

Additional acetonitrile (100 mL) was added and distillation continued to a final volume of 70 mL.

NMR assay indicated that the MeOH was removed.

The batch was diluted to 110 mL total volume with acetonitrile and water (150 mL) was added slowly (~1.5 h) at about 20° C.

It is best to charge approximately 30% of the total volume of water, seed, and then allow the resulting slurry to age for about 30 min before adding the remaining water. Optimization of the crystallization has shown that the yield and purity are sensitive to the acetonitrile:water ratio. Karl Fisher moisture determination of the mother liquors at the end of the water additions should indicate approximately 60–62% water.

If the water content is too low (i.e., <60%), the yield will suffer (i.e., >10% losses). If the water content is too high (i.e., >62%), the purity will be lower.

After aging for 12 hours, the product was filtered, washed with acetonitrile/water (1:2, 25 mL) and then dried under an air sweep for 12 hours to give 14.5 g of white solid (92%).

The product was isolated as a hydrate (12% water). HPLC assay typically showed >98 A % product. Chiral analysis typically shows approximately 98% ee.

The free base was dissolved in acetonitrile (116 mL) at 20° C. and water (174 mL) is added slowly over 1.5 h.

As above, it is best to add approximately 30% of water, seed and age the slurry for approximately 30 min before charging the remaining water.

The slurry was aged for 12 h at 20° C. and filtered. The cake was washed with acetonitrile:H20 (1:2, 25 mL) and dried in vacuo to provide 13.05 g (90%) of the alcohol free base.

The product was typically >99 A % pure and chiral assay indicated >98.5%. The final product was assayed using HPLC under the following conditions:

1) Macherey-Nagel Nucleosil® C18 CH$_3$CN:H$_2$O:0.1% H$_3$PO$_4$ Gradient=15:85 to 40:60 (20 min) to 90:10 (30 min), 1.0 μL/min 220 nm
2) Zorbax Rx-C8, CH$_3$CN:H$_2$O:0.1% H$_3$PO$_4$ Gradient= 15.85 to 50:50 (25 min)

Chiral analysis is conducted using:
Waters μ-Bondapak C18;
MeOH:H$_2$O:0.1% H$_3$PO$_4$, 1.25 mL/min, 220 nm

What is claimed is:

1. A process for the production of spirocycles of Formula I wherein the process results an alcohol having an enantiomeric efficiency of 98% or higher

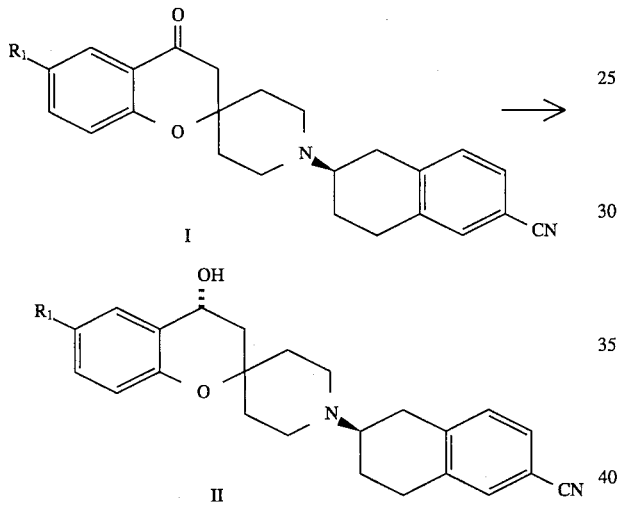

where $R_1$ is selected from the group consisting of CO—$C_{1-3}$ alkyl, cyano, carboxy, carboxy $C_{1-6}$ alkyl ester, carboxamido, $C_{1-6}$ alkyl sulfinyl, $C_{1-6}$ alkyl sulfonyl, $C_{1-6}$ methansulfamido and halogen; comprising the steps of:

(1) adding the benzylic ketone to methylene chloride in a ratio of about 0.032 moles of the benzylic ketone to 300 mL of methylene chloride and stirring to produce a slurry;
(2) adding 5% aqueous sodium bicarbonate at a ratio of about 163 mL for every 0.032 moles of the benzylic ketone to the slurry and maintaining the temperature at about 20°–25° C.;
(3) Stirring the mixture of step (2) for about 60 minutes;
(4) Allowing the mixture of step (3) to settle;
(5) Separating the organic layer of step (3) and washing it with half saturated brine;
(6) Concentrating the methylene chloride phase by atmospheric distillation to a final volume of approximately 90% of the initial volume of methylene chloride used in step (1);
(7) Cooling the solution of step (6) to about −18° C.;
(8) Adding a molar amount of borane methyl sulfide equal to about 2.4 times the molar mount of benzylic ketone of step (1) and adding a molar amount of isopropanol equal to from 1 to 3 times the number of moles of the benzylic ketone added in step (1);
(9) Adding oxazaborolidine.BH$_3$ complex as a solid and stirring the reaction for about 25 minutes at about −18° C.;
(10) Gradually increasing the temperature to about 18° C. over about 35 minutes;
(11) Stirring for about 45 to 60 minutes until the reaction is complete;
(12) Adding methanol and mixing at about 18° C. for about 30 minutes;
(13) Distilling off methyl sulfide, methylene chloride and trimethylborate, with heat;
(14) Adding additional methanol and heating to 63°–65° C. for 35 minutes to decompose the amine borane complex;
(15) Adding acetonitrile and vacuum distillating to remove the methanol;
(16) Adding water to the acetonitrile solution and seeding with authenetic crystals of the compound of Formula II to begin crystallization; and
(17) Collecting the crystals of Formula II by filtration.

2. The method of claim 1 wherein the benzylic ketone is the

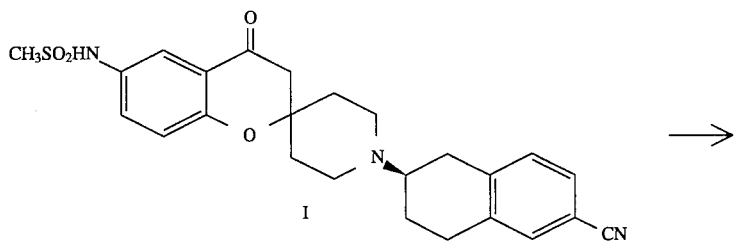

-continued
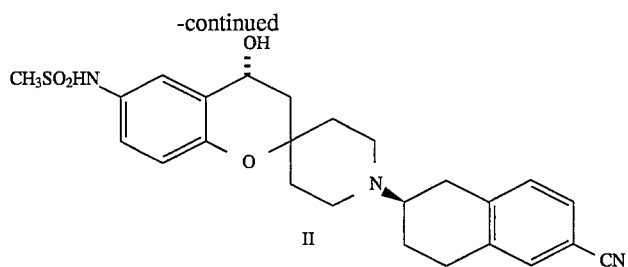
II
compound of Formula I which is reduced to the compound of Formula II.
* * * * *